United States Patent [19]

Bonnell

[11] Patent Number: 5,779,623

[45] Date of Patent: Jul. 14, 1998

[54] POSITIONER FOR MEDICAL INSTRUMENTS

[75] Inventor: Leonard J. Bonnell, Huntingdon Valley, Pa.

[73] Assignee: Leonard Medical, Inc., Huntingdon Valley, Pa.

[21] Appl. No.: 564,772

[22] Filed: Nov. 29, 1995

Related U.S. Application Data

[63] Continuation-in-part of Ser. No. 134,206, Oct. 8, 1993, Pat. No. 5,540,649.

[51] Int. Cl.$^6$ .............................. A61B 1/01; B65H 51/18
[52] U.S. Cl. .................... 600/114; 600/102; 414/431; 414/746.7
[58] Field of Search .................... 600/102, 114; 604/156, 164, 30; 606/130; 414/431, 432, 746.7, 745.1, 745.2; 227/30, 124, 125, 126; 901/41; 226/186, 187, 188, 185, 181; 254/30, 396, 295, 298; 294/106

[56] References Cited

U.S. PATENT DOCUMENTS

| | | |
|---|---|---|
| 1,537,545 | 5/1925 | Morton . |
| 2,838,953 | 6/1958 | Cone ........................................ 226/187 |
| 2,948,513 | 8/1960 | Krohn-Holm ........................... 254/396 |
| 3,871,618 | 3/1975 | Funk . |
| 4,054,128 | 10/1977 | Seufert et al. ............................ 600/116 |
| 4,184,510 | 1/1980 | Murray et al. . |
| 4,206,664 | 6/1980 | Miyagawa ................................ 82/113 |

(List continued on next page.)

FOREIGN PATENT DOCUMENTS

| | | |
|---|---|---|
| 483721 | 8/1917 | France . |
| 3710296 | 10/1988 | Germany . |
| 392126 | 4/1991 | Japan . |

OTHER PUBLICATIONS

Munro, "Automated Laparoscope Positioner: Preliminary Experience", Journ. Am. Ass. Gyn. Lap., vol. 1, No. 1, Nov. 1993, pp. 67–70.

Translation of Japan Pat. 3-92126 (Apr. 1991) Cited in Previous Office Action).

ENDEX brochure, Endex Endoscopy Positioning System, Advancing the scope of endoscopy, Apr. 1993.

AESOP brochure, "Get an Extra Hand with Your Procedures with Robotics", 1993.

M. Moran, "Stationary and Automated Laparoscopically Assisted Technologies", 1993, *J. Laparoendoscopic Surgery*, vol. 3, No. 3, pp. 221–227.

G. Berci, et al., "New Ideas and Improved Instrumentation for Laparoscopic Cholecystectomy", 1991, *Surgical Endoscopy*, No. 5, pp. 1–3.

A. Cuschieri, "Minimal Access Surgery and the Future of Interventional Laparoscopy", Mar. 1991, *Amer. J. Surgery*, vol. 161, pp. 404–407.

L. K. Nathanson, et al., "Laparoscopic Cholecystectomy: the Dundee Technique", Feb. 1991, *Br. J. Surg.*, vol. 78, pp. 155–159.

Leonard Medical, Inc., "Instrument Control: Manageable and Tireless", Apr., 1993, Brochure.

Leonard Medical, Inc., "Instrument Control: Manageable and Tireless", Apr., 1993, Leonard Arm U.S. Patent No. 4,863,133.

*Primary Examiner*—John P. Leubecker
*Attorney, Agent, or Firm*—Fish & Richardson P.C.

[57] ABSTRACT

A remote-controlled device is capable of selectively positioning a medical instrument within a predetermined region of space. The device includes a clamp having two pivotally mounted sections enabling the clamp to be placed in either an opened position or a closed position. Each section has a drive wheel including an arc-shaped groove which accommodates the medical instrument when the clamp is placed in the closed position. Each of the wheels has a coupling gear positioned and configured to pivot apart when the clamp is placed in the open position with portions of teeth of the gears remaining engaged with each other. One of the drive wheels is directly driven by a motor housed in one of the sections of the clamp.

20 Claims, 9 Drawing Sheets

U.S. PATENT DOCUMENTS

| | | |
|---|---|---|
| 4,229,136 | 10/1980 | Panissidi . |
| 4,517,963 | 5/1985 | Michel . |
| 4,566,358 | 1/1986 | Ducanis . |
| 4,616,648 | 10/1986 | Simpson .................................. 604/159 |
| 4,652,204 | 3/1987 | Arnett . |
| 4,659,280 | 4/1987 | Akeel . |
| 4,784,010 | 11/1988 | Wood et al. . |
| 4,856,354 | 8/1989 | Overbay . |
| 4,863,133 | 9/1989 | Bonnell . |
| 4,881,709 | 11/1989 | Nakamura . |
| 5,018,509 | 5/1991 | Suzuki et al. . |
| 5,054,725 | 10/1991 | Bucefari et al. . |
| 5,104,103 | 4/1992 | Auchinlek et al. . |
| 5,154,723 | 10/1992 | Kubota et al. . |
| 5,184,601 | 2/1993 | Putman . |
| 5,184,603 | 2/1993 | Stone . |
| 5,205,522 | 4/1993 | Nakamura . |
| 5,243,967 | 9/1993 | Hibino . |
| 5,251,156 | 10/1993 | Heier, et al. . |
| 5,253,845 | 10/1993 | Wilbert ..................................... 254/30 |
| 5,265,634 | 11/1993 | Chapman et al. ....................... 134/181 |
| 5,282,472 | 2/1994 | Companion et al. . |
| 5,318,442 | 6/1994 | Jeffcoat et al. ......................... 128/776 |
| 5,318,541 | 6/1994 | Viera et al. . |
| 5,380,338 | 1/1995 | Christian ................................ 606/130 |

POSITIONER FOR MEDICAL INSTRUMENTS

RELATED PATENT APPLICATIONS

This patent application is a continuation-in-part of patent application Ser. No. 08/134,206, filed Oct. 8, 1993, now U.S. Pat. No. 5,540.

BACKGROUND

This invention relates to devices for positioning medical instruments.

Surgical procedures, e.g., those involving minimally invasive endoscopic surgery, require simultaneous use of numerous instruments by a physician. Often the procedure is complicated and one or more assistants may be required to hold one or more of these instruments in position. These assistants tend to congest the area around the operating table and restrict movement by the physician performing the surgery.

To address this problem, arms to hold surgical equipments have been suggested. For example, Bonnell (1989, U.S. Pat. No. 4,863,133, by one of the inventors here) discusses an articulated instrument support arm that employs vacuum switch controls to set the position of the arm with lightly loaded restraint. Milo (1975, U.S. Pat. No. 3,858,578) describes a flexible arm for holding surgical instruments, the joints of which can be simultaneously locked in place, using hydraulic pressure to tension a cable extending axially through the assembled arm elements. Poletti (1972, U.S. Pat. No. 3,638,973) and Kimoshita (1976, U.S. Pat. No. 3,986,692) describe jointed arms which can be fixed in position by hydraulic pressure.

SUMMARY

In general, in one aspect, the invention features a remote-controlled device for selectively positioning a medical instrument within a predetermined region of space. The remote-controlled device has a motor which provides mechanical energy to the remote-controlled device, a driver that is coupled to the motor and that has a predetermined relationship with the motor. The driver physically engages the medical instrument and converts the mechanical energy into controlled motion of the medical instrument. The remote-controlled device receives control signals from a remote location that direct the motor to supply a predetermined amount of mechanical energy, whereby the driver, with the predetermined relationship with the motor, selectively positions the medical instrument within the region of space.

At various times during surgery, a surgeon will require that a surgical instrument be repositioned. The invention permits the surgeon to act as an orchestra leader, directing his or her surgical team through a procedure, by providing a surgeon with the ability to precisely position an instrument, e.g., a powered surgical instrument or an endoscopic camera, for a surgical procedure from a remote location, allowing the surgeon to leave the vicinity of the instrument and to position himself or herself at various desired locations around the patient. The invention further permits the surgeon to precisely position the instrument by means of a foot control or some other controlling mechanism that frees the surgeon from having to position the instrument manually. The surgeon is permitted to use the freed hand for some other purposes, e.g., to better employ tactile control or monitoring of the patient, e.g., in positioning or manipulating the limbs.

Embodiments of the invention may include one or more of the following features. The device is remote-actuated by a foot-controlled switch. The device is remote-controlled by an electromagnetic-wave (e.g., infrared or RF radiation) transmitter. The device is steam-autoclavable. The controlled motion of the device is in a longitudinal direction.

The device is a clamp having two pivotally mounted sections enabling the clamp to be placed in either an opened position or a closed position. Each section has a drive wheel, or roller. Each wheel has an arc-shaped groove disposed about its outer surface in a plane perpendicular to the axis of rotation of the wheel. When in an open position, the outer surfaces of the sections, and therefore the outer surfaces of the drive wheels, are adapted to pivot apart at the distal end of the clamp sufficient to permit the instrument shaft, here the shaft of the endoscope, to pass between, and be received in a region between the pair of drive wheels. When in the closed position, the two sections come together and opposing portions of the arc-shaped grooves grasp opposing outer portions of the surface of the received instrument shaft. Each one of the wheels has a coupling gear. When in the closed position, the drive wheels are adapted to drive the grasped instrument shaft in response to rotation of the drive wheels about the axis of rotation. A primary one of the drive wheels is directly driven by a motor housed in one of the sections of the clamp. The coupling gears are positioned and configured to pivot apart when the clamp is in the open position with portions of teeth of the gears remaining engaged with each other thereby preventing the gears from becoming misaligned when the clamp is placed in the closed position. Thus, as the clamp is placed in the closed position, teeth of the coupling gears become meshed to a greater extent than when in the open position and the drive wheels are mechanically coupled together through more complete engagement of the teeth of the coupling gears.

An eccentric cam, pivotally mounted to one of the sections of the clamp is used to lock the meshed gears of pair of drive wheels in place. More particularly, to place the clamp in the closed position, the cam is rotated and a camming surface thereof is urged against the other one of the sections to cause such other section to rotate its distal end towards the cam mounted section and, after completion of rotation of the cam, thereby lock the clamp in the closed position. Alternatively, the two sections may be manually brought together and then locked into the final closed position by the described camming action.

In a preferred embodiment, the arc of each arc-shaped drive wheel extends for 30–35 degrees thereby enabling the drive wheels to distribute the driving load over a relative large area of the outer instrument shaft as distinguished from stainless steel drive wheels which engage the shaft at only contact points. More particularly, it has been found that with endoscopes having shaft wall thicknesses of about 0.006 inches, stainless steel drive wheels which engage the shaft at only contact points, the amount of radial force required to axially drive the shaft without slippage deform the shaft and form grooves along its length.

The portions of the drive wheels which grasp the shaft is a material having a durometer of between 40–60, preferably a durometer of 50. The material is adapted to survive 200 stream autoclaves cycles without significant degradation. Preferably, the material is Viton silicon based rubber. The relevant factors in selecting the durometer of the material are the driving load, the area over which the load is distributed about the shaft, and the wall thickness of the shaft. If too low a durometer is used, the material tends to grip too much and the material tends to rip apart; if too high a durometer is used, the radial force required to drive the endoscope shaft without slippage is so high that the endoscope shaft becomes damaged.

The invention permits the surgeon to be his or her own camera operator, when employed with an endoscopic camera (e.g., a laparoscope). This is very important since usually only the surgeon knows exactly what she is looking at, and time-consuming communication between the surgeon and a camera operator may be avoided, thereby reducing the overall time required to complete a surgical procedure. The invention is easy to operate and allows remote-controlled adjustment of the camera position to achieve e.g., optimal framing (e.g., centering on the most important part of the surgical field and adjusting the relative degree of closeness to the surgical field) of the picture, while remaining far less obtrusive to the operating surgeon than having another person operating the camera, who would likely impede access to the surgical site.

Because the invention is steam-autoclavable, the invention may be used in a surgical environment without requiring the use of space-consuming and view-obstructing protective plastic bags, or the like.

In general, in another aspect, the invention includes the features of a remote-controlled device for selectively positioning a medical instrument within a predetermined region of space which includes an instrument-supporting, articulated support arm. The arm has a distal end capable of supporting an instrument in the region of a surgical operating site and has at least one joint that supports a movable distal support element relative to a proximal support. The joint is associated with a mode selector. The remote-controlled device is coupled to the distal support element of the support arm.

When used in conjunction with a support arm, the invention permits the surgeon to leave the surgical area, e.g., to consult with other surgeons who may not be prepared to enter the surgical area, while being able to maneuver e.g., an endoscopic camera to achieve different views of the patient, if desired.

Embodiments of the invention may also include the following features. The support arm has structure capable, upon selection of a first mode of operation by the selector, of enabling relatively free motion of the joint for achieving a desired position of the medical instrument. The joint has structure capable, upon selection of a second mode of operation by the selector, to set the position of the instrument in space with lightly loaded restraint.

DESCRIPTION

FIGS. 6A through 6C are sketches of drive device according to the invention.

FIGS. 7A and 7B are somewhat simplified cross sectional views of the device of FIGS. 6A–6C; FIG. 7A showing the device in the closed position and FIG. 7B showing the device in the open position.

FIGS. 7C and 7D are views of a portion of the interior region of the device of FIGS. 6A–6C; FIG. 7C showing the device in the closed position and FIG. 7D showing the device in the open position.

Figure 1:
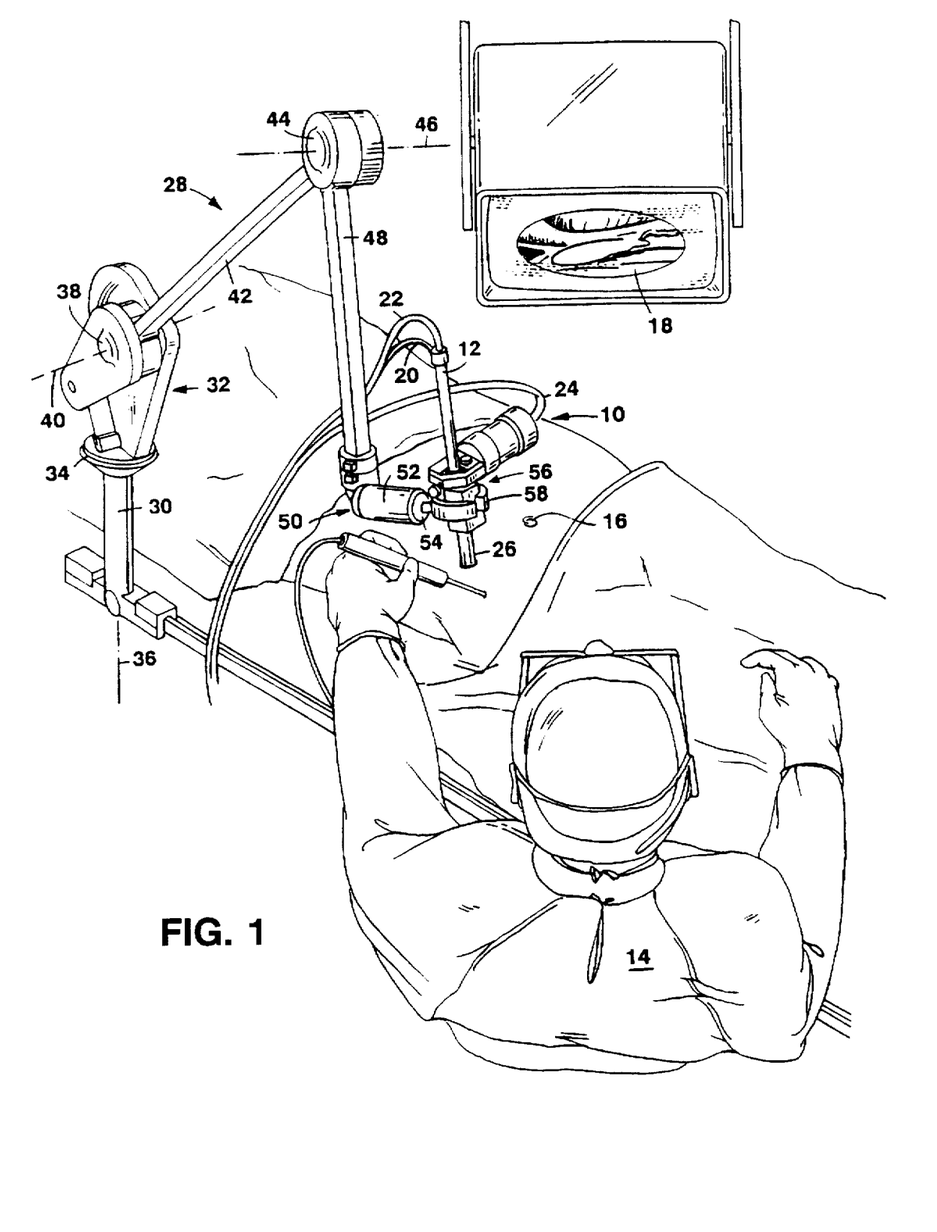
FIG. 1 is a somewhat diagrammatic perspective view of a surgeon employing the instrument-positioning device of the invention for positioning an instrument during surgery, e.g., on a patient's abdomen.

Referring to FIG. 1, an instrument-positioning device 10 of the invention is coupled to an endoscopic camera 12 (e.g., a laparoscope which has a shaft with a length of about 35 cm and outer diameter of about 10 mm), and allows a surgeon 14 to remotely control the position of the laparoscope at a desired location about the surgical site, e.g., as shown in the figure, a patients abdomen 16, or other space, to achieve a desired view from inside the body on a video monitor 18. The source of illumination for the camera is supplied by a fiberoptic cable 20, while the image signals from the camera are carried on a cable 22. Cable 24 delivers control signals from a foot-operated, wet-cell rechargeable battery, DC power source (FIG. 4) to the instrument-positioning device. The control signals direct the instrument-positioning device to selectively position the laparoscope in and out of a cannula 26 to achieve narrower and wider fields-of-view on monitor 18.

The instrument-positioning device 10 and the cannula 26 are held fixedly in a desired position by a support arm 28, e.g., a Leonard Arms™ available from Leonard Medical of Huntingdon Valley, Pa., U.S.A., described in U.S. Pat. No. 4,863,133, issued to Bonnell (a co-inventor here) on Sep. 5, 1989, the entire disclosure of which is hereby incorporated by reference herein. The support arm consists of a vertical support post 30, a shoulder assembly 32 constructed for rotation at 34 about axis 36 and including shoulder joint 38 constructed for rotation about axis 40; upper arm 42; elbow joint 44 constructed for rotation about axis 46; forearm 48; and wrist assembly 50, including a wrist joint 52, e.g., a pair of spherical joints adapted to swivel independently of each other. At the end of the wrist assembly there is provided a quick disconnect assembly 54 for receiving an instrument clamp 56.

Figure 2:
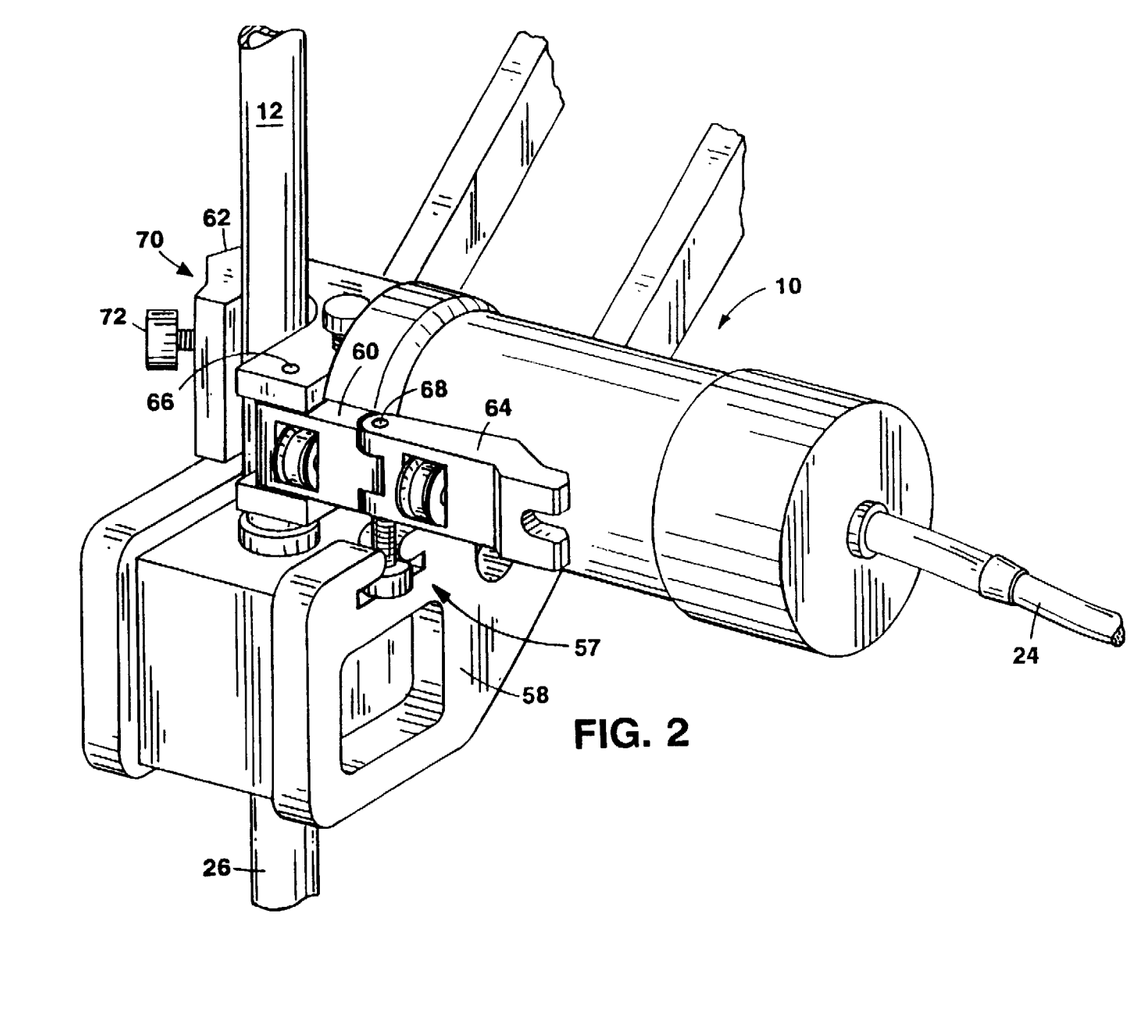
FIG. 2 is a perspective side view of an instrument-positioning device.

The cannula 26, extending through a puncture in the flesh to provide a conduit into a region of the body, e.g., the abdomen or knee, is gripped by the jaws 58 of clamp 56, while the instrument-positioning device is attached to the gripper by means of a boutonniere pin arrangement 57 (FIG. 2). Because the actuator is attached to the gripper at the end of the wrist assembly, the actuator is allowed to follow the motion of the laparoscope, accommodating any reasonable shift of the laparoscope without change in performance.

The instrument-positioning device is designed to attach onto a support arm after the laparoscope is in place, which allows the surgeon freedom to grossly position the laparoscope about the surgical site before attaching the actuator. The instrument-positioning device is roughly cylindrical and as small as practical, and, e.g., in the embodiment shown, the device has with a diameter of about ¾-inch to 1 inch and a length of about 5–7 inches. For example, during a Nissen fundoplication, it may be necessary for a surgeon to reposition the angle of the laparoscope relative to the patient, and a large attachment to the laparoscope would interfere with the patient's body and thereby limit the mobility range of the laparoscope (and thus the surgeon's viewing range inside the patient). In addition, a large attachment to the laparoscope would obscure the surgeon's view of the surgical site.

As shown in FIG. 2, the actuator attaches to the laparoscope using a three-bar linkage mechanism including a proximal link 60, a main bracket 62, and a distal link 64. Proximal link 60 is attached to main bracket 62 via a proximal pivot point 66 that allows the proximal link to pivot away from the laparoscope 12. Similarly, distal link 64 pivots about the proximal link at a distal pivot point 68. The distal link attaches to the distal end 70 of main bracket 62 by a retention element 72, e.g., a screw or lever.

The instrument-positioning device may be freely removed without disturbing the laparoscope by releasing the retention element to and allow the distal link to pivot about the proximal link, and simultaneously permitting the proximal link to rotate about the proximal pivot point.

Figure 3:
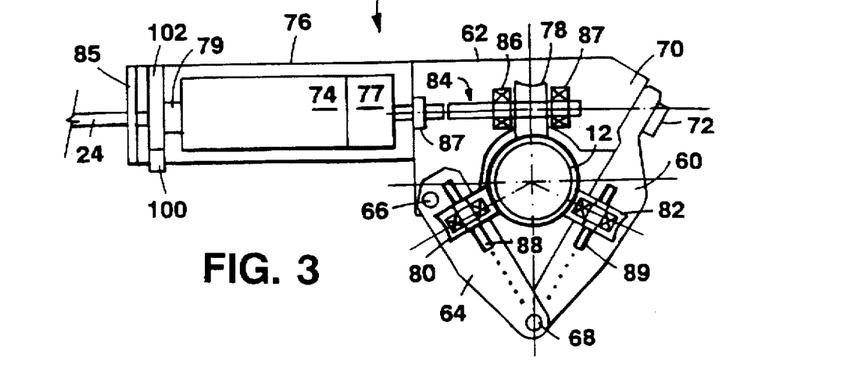
FIG. 3 is a schematic top view of an instrument-positioning device.

Referring to FIG. 3, instrument-positioning device 10 has a motor 74, a motor housing 76, a gear head 77 (e.g., a 200:1, or alternatively, a 100:1) gear head 77, main bracket 62, proximal and distal links 60 and 66, respectively, a drive wheel 78, and proximal and distal support wheels 80, and 82, respectively.

The instrument-positioning device employs three stainless steel wheels, which press firmly against the shaft of the laparoscope, to selectively position the laparoscope. The wheels are equally spaced around the laparoscope shaft (i.e. the wheels are spaced 120° apart) to provide a balanced load, and frictionally drive the scope. That is, static friction transfers the rotational motion of the wheel into lateral motion of the scope. There is a direct and important relationship between the maximum driving force and the normal force of the wheel against the laparoscope. The greater the normal force, the greater the driving force. The practical limit is the compressional strength of the laparoscope itself.

Drive wheel 78 is coupled to motor 74 via a stainless steel coupler (drive shaft) 84. Stainless steel, high-temperature, sealed ball bearings 86 and 87 rigidly hold the drive wheel in place on the shaft. Proximal and distal support wheels are mounted on springs 88 and 89 for flexibly pressing the wheels against the outer wall of laparoscope 12 to provide a force (pre-load) of about 20 pounds against the laparoscope. (A greater force may damage the laparoscope, while a lesser force would not provide the necessary retention force to withstand the normal dynamic loads on the laparoscope, e.g., tension transmitted to the laparoscope from movement of the camera cable 22.)

The drive wheel and the two support wheels have each been machined with a "V" groove to provide two points of contact between the outside surface of the wheel and the laparoscope. Because the normal force is applied across two points for each wheel, rather than at one point, e.g., a flat roller wheel, the instrument-positioning device 10 may accommodate high load levels.

Motion of the laparoscope is achieved with a miniature DC electric motor 74 adapted to run in either direction, thus permitting forward and reverse motion of the laparoscope. The gear train (e.g., motor 74 and gear head 77) additionally provides resistance to slippage. Without the motor's internal friction, the drive wheel would not be "braked" and the laparoscope would be free to move in and out of the cannula. The force required to overdrive the gear train is sufficiently high to prevent unintentional movement of the scope. The force is also sufficiently low that if the laparoscope is forcibly withdrawn from the instrument-positioning device, the gears are driven without any damage to the actuator mechanism.

In a preferred embodiment, a dynamic brake 79 is added to provide further resistance to slippage of the laparoscope. For example, the brake 79 may include a conventional switch located within the motor housing 76. When activated, the switch creates a short circuit across the windings of DC motor 74, immediately stopping the rotation of the motor and thereby preventing the laparoscope from drifting.

The internal parts of the instrument-positioning device are sealed from the external environment by a static o-ring seal 85 and a high-temperature sealed bearing 87, which allows the device to be steam autoclaved, thereby permitting the device to be employed in a surgical site without requiring it to be sealed inside a plastic bag or other protective covering.

Figure 4:
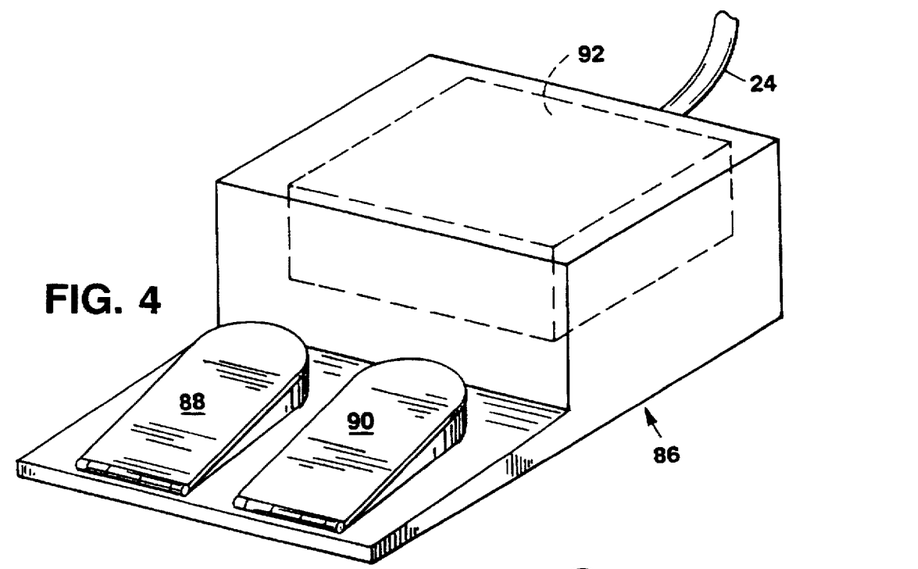
FIG. 4 is a schematic view of a remote actuator for use with the instrument-positioning device.
Figure 5:
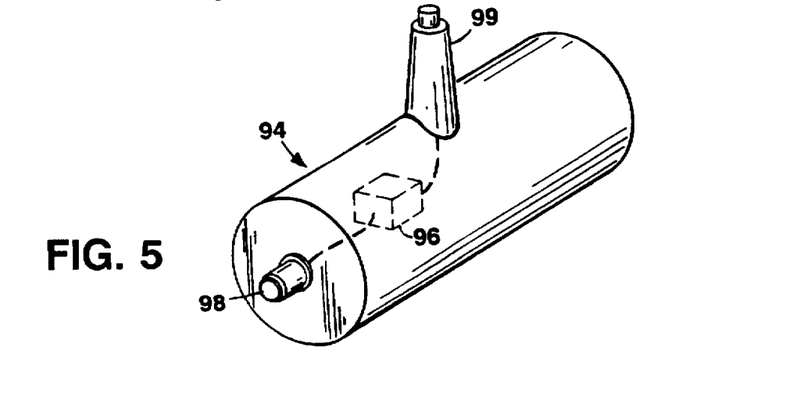
FIG. 5 is a somewhat perspective view of a remote actuator for use with the instrument-positioning device.

Referring to FIG. 4, the motor 74 is driven by one of many possible means in parallel. The primary remote actuator is a foot-activated controller 86. A pedal 88 acts as a switch to couple cable 22 in a forward polarity configuration to a wet-cell, rechargeable battery source 92, which when activated causes a forward polarity signal to be sent to the instrument-positioning device 10 that causes motor 74 to drive the laparoscope further into the cannula for a close-up view of the surgical area. A pedal 90 acts in a similar manner as pedal 88, except that pedal 90 couples cable 22 to the battery source in a reverse polarity configuration that causes motor 74 to drive the laparoscope out of the cannula.

The instrument-positioning device may also be controlled by an infrared control signal. The instrument-positioning device operates in forward or reverse direction depending on the frequency of the infrared signal. A remote transmitting device 94 is designed to be used by either the surgeon or an assistant, and may be attached, e.g., by means of a VELCRO® strap, to the shaft of a medical instrument to be used by the surgeon during a surgical procedure. Similar to a television remote control, the transmitter has a frequency generator 96 which drives a transmitter 98. The transmitter is cylindrical with a diameter of about ¾-inch and a length of about 1 inch. A thumb-activated control joy-stick 99 is disposed on the shaft of the transmitter to selectively generate forward or reverse control signals.

Built into the motor drive is an infrared diode receiver 100 (FIG. 3). This component receives the transmitted optical signal, converts it into electrical frequency which is fed to a decoder 102. The decoder determines the specific frequency and drives the appropriate motor relay. For either frequency, the motor activated as long as the signal is present.

Figure 6A:
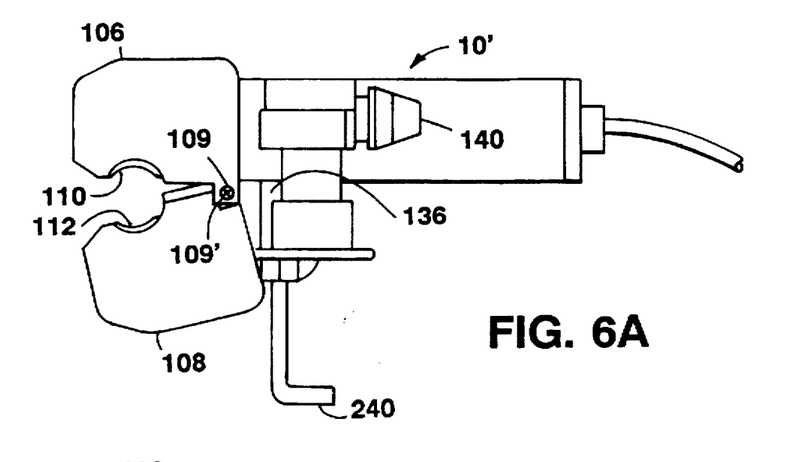
FIG. 6A is a top elevation view of the device in an open position.
Figure 6B:
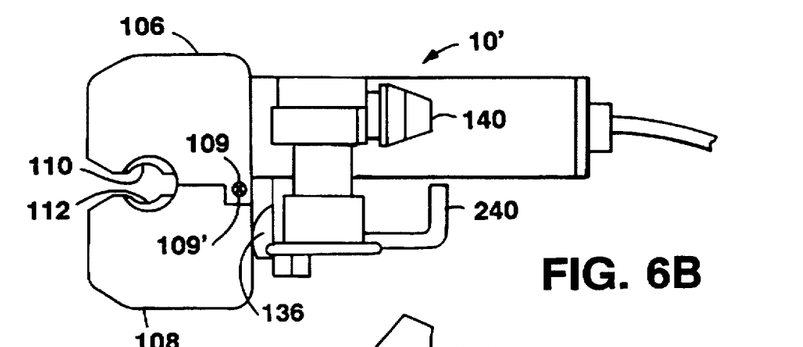
FIG. 6B is a top elevation view of the device in a closed position.
Figure 6C:
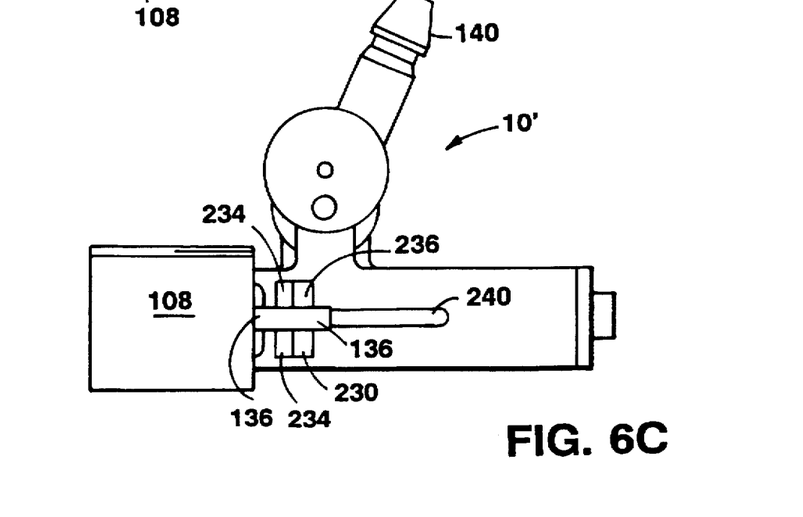
FIG. 6C is side elevation view of the device in a closed position.
Figure 7A:
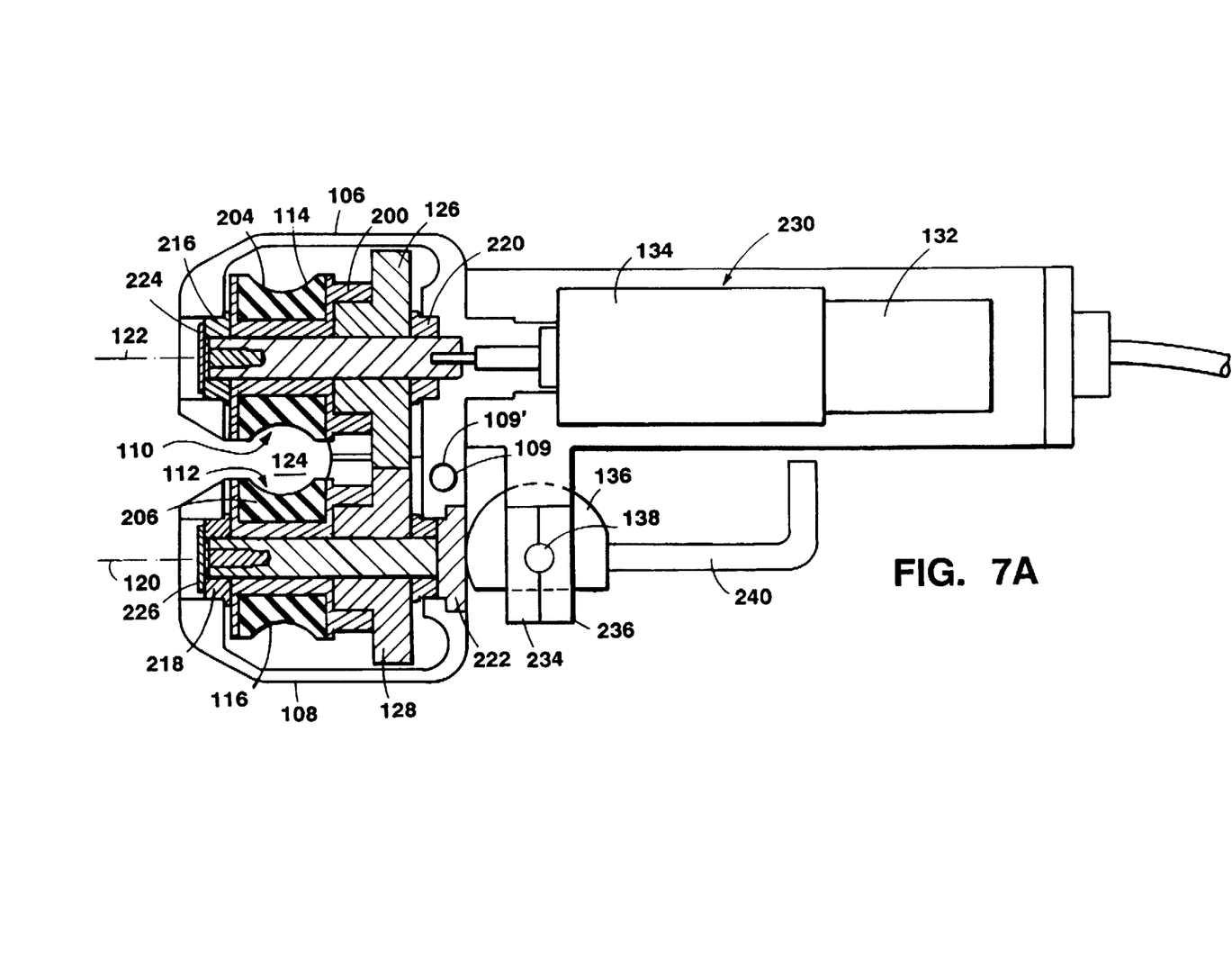
Figure 7B:
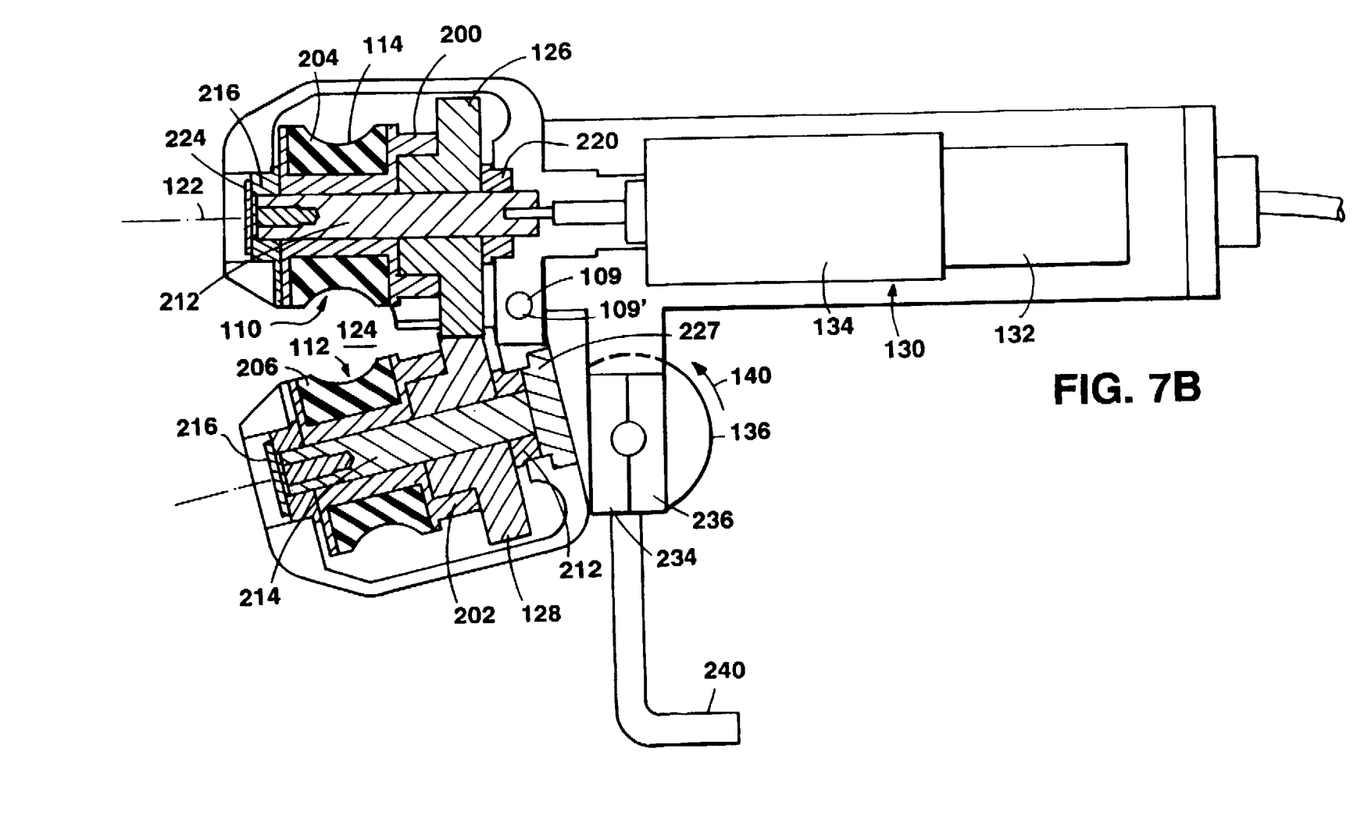
Figure 7C:
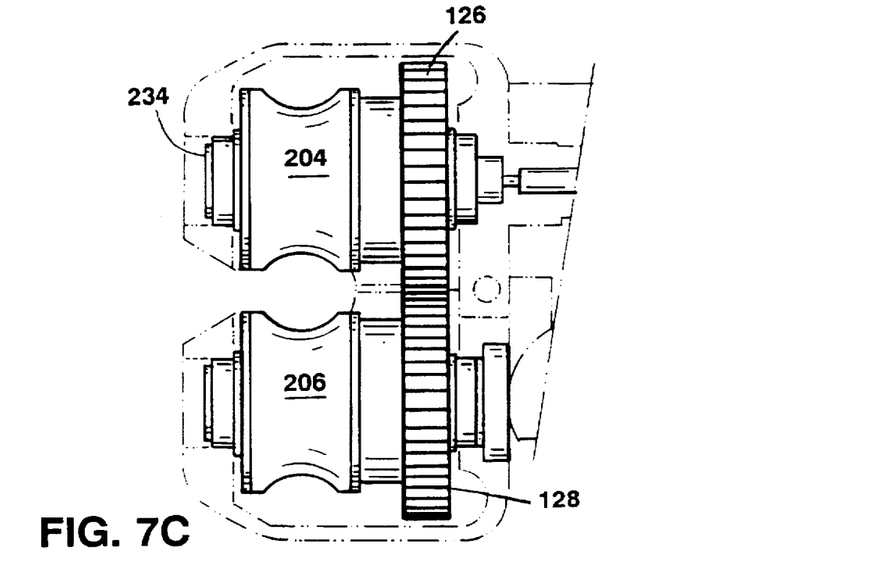
Figure 7D:
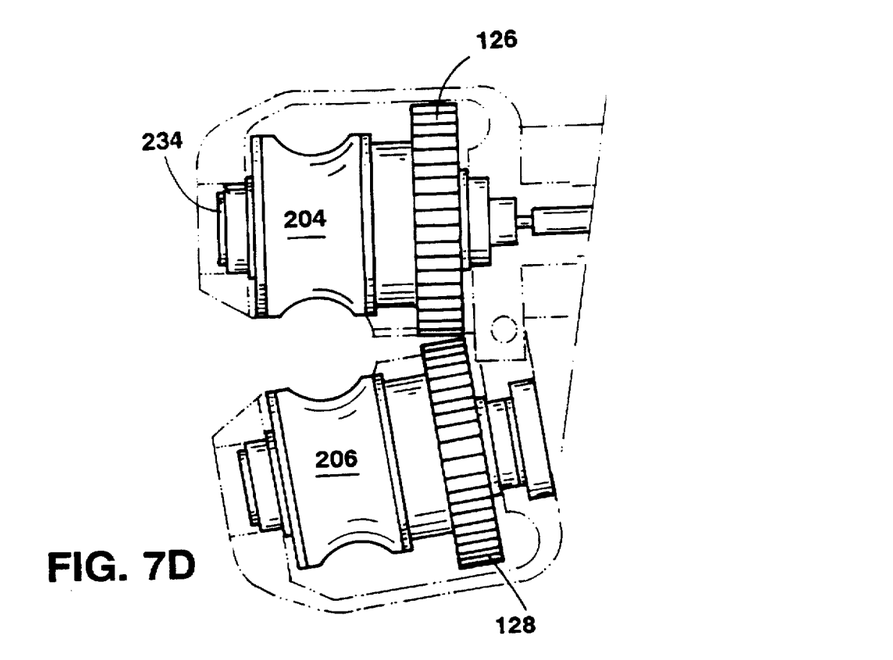

Referring now to FIGS. 6A, 6B, and 6C, an instrument-positioning device 10' is shown; FIG. 6A showing the device 10' in the open position and FIG. 6B showing the device 10' in the closed position. The device 10' is thus a clamp having two sections 106, 108 mounted to pivot about axis 109 thereby enabling the clamp 10' to be placed in either an opened position or a closed position. Each section 106, 108 has a corresponding one of a pair of drive wheels 110, 112, or rollers, shown more clearly in FIGS. 7A, 7B, 7C and 7D; FIGS. 7A and 7C showing the device 10' in the closed position and FIGS. 7B and 7D showing the device in the opened position. Each wheel 110, 112 has an arc-shaped groove 114, 116, respectively, disposed circumferentially about its outer surface in a plane perpendicular to the axis 120, 122, respectively, of rotation of the wheel 110, 112, respectively. Here, the arc of each arc-shaped drive wheel 110, 112 extends for 30–35 degrees thereby enabling the drive wheels 110, 112 to distribute the driving load over a relative large area of the outer instrument shaft 12 as distinguished from drive wheels which engage the shaft at only contact points.

When in an open position, the outer surfaces of the sections 106, 108, and therefore the drive wheels 110, 112, are pivoted apart at the distal end of the clamp 10' sufficient to permit the instrument shaft 12 (FIGS. 1 and 3), here the shaft of the endoscope, to pass between such wheels 110, 112, and be received in a region 124 between the pair of drive wheels 110, 112. When in the closed position, the two sections 106, 108 pivot about axis 109 and come together and opposing portions of the arc-shaped grooves 114, 116 grasp opposing outer portions of the surface of the received instrument shaft 12.

Each one of the wheels 110, 112 has a coupling gear 126, 128, respectively, as shown. When in the closed position, the drive wheels 110, 112 are adapted to drive the grasped instrument shaft 12 in response to rotation of the drive wheels 110, 112 about the axis of rotation 122, 122, respectively. A primary one of the drive wheels 110, 112, here drive wheel 110, is directly driven by a motor assembly 130, here made up of a motor 132 and its gear train 134. The motor assembly 130 is housed in one of the sections 106, 108, here section 106 of the clamp 10'. The coupling gears 126, 128 are positioned and configured to pivot apart in the when the clamp 10' is in the open position with portions of teeth of the gears 126, 128 remaining engaged with each other thereby preventing the gears 126, 128 from becoming misaligned when the clamp 10' is pivoted into the closed position. Thus, as the clamp 10' is placed in the closed position, teeth of the coupling gears 126, 128 become meshed to a greater extent than when in the open position and the drive wheels 126, 128 are more securely mechanically coupled together through more complete engagement of the teeth of the coupling gears 126, 128.

An eccentric cam 136, mounted to section 106, is adapted to rotate, or pivot, about axis 138 and is used to lock the sections 106, 108, and therefore the meshed gears of pair of drive wheels, in place when the clamp 10' is in the closed position. More particularly, to place the clamp 10' in the closed position, the cam 128 is rotated about axis 138 in the direction of the arrow 140 in FIG. 7B and a camming surface 142 of cam 128 is urged against the other one of the sections, here section 108, to cause such other section 108 to rotate its distal end towards the cam mounted section 106 and, after completion of rotation of the cam 136, thereby lock the clamp 10' in the closed position, as shown in FIG. 7A.

Referring again to FIGS. 6A-6C, it shown be noted that the clamp 10' includes a stem 140 having a distal end 142 adapted for insertion into the quick disconnect assembly 54 (FIG. 1). The stem 140 is adapted to pivot about a shaft 143.

Figure 8:
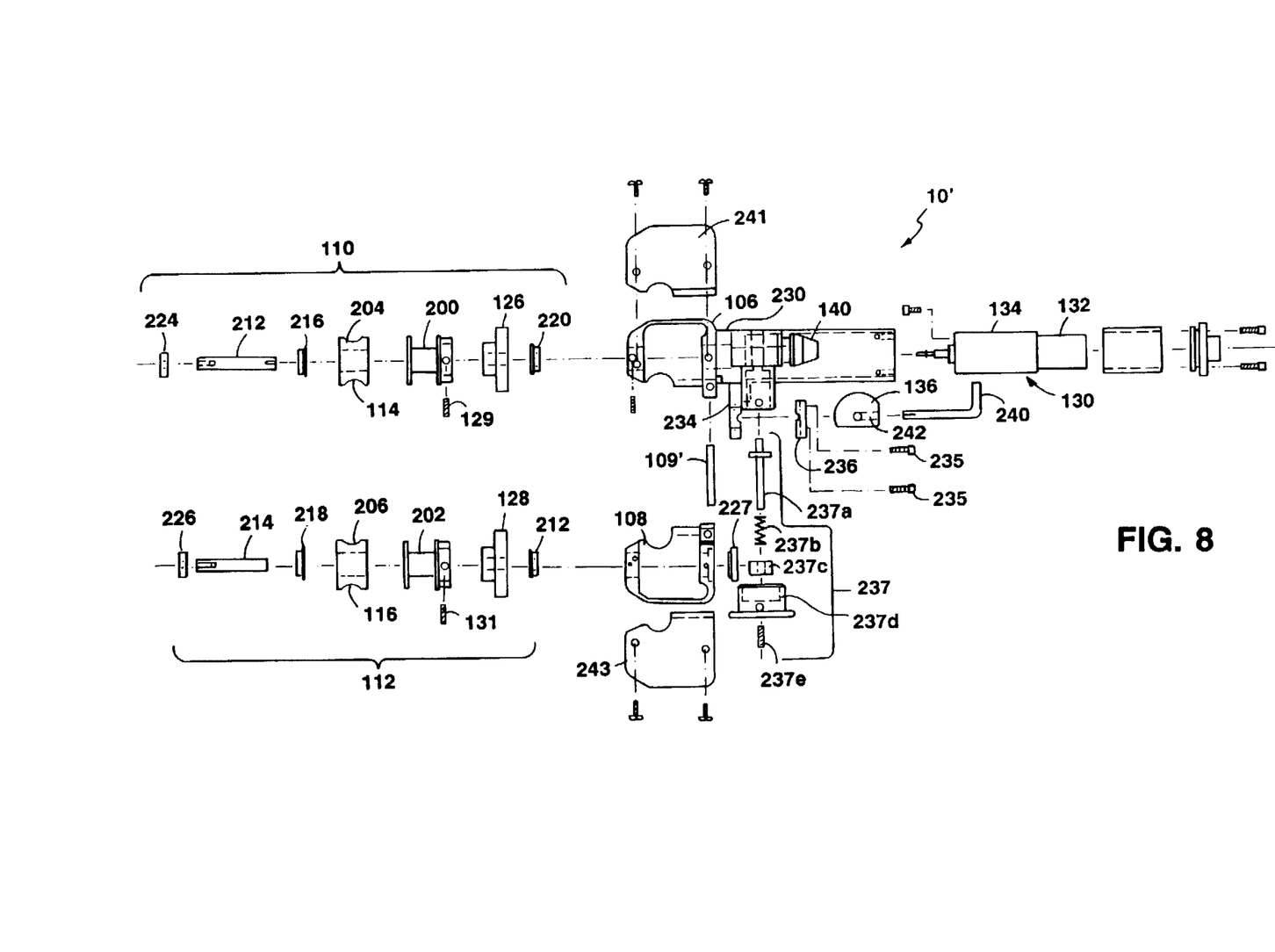
FIG. 8 is an simplified, two-dimensional exploded view of the device of FIGS. 6A–6C.

Referring now to FIG. 8, the two dimensional assembly drawing shows the clamp 10' in more detail. Thus, the wheels 110, 112 each includes a core roller 200, 202, respectively, having molded thereon a rubber roller 204, 206, here a silicone based rubber having a durometer in the range of 40 and 60, here 50. Here the silicone based rubber is Viton rubber. The relevant factors in selecting the durometer of the material are the driving load, the area over which the load is distributed about the shaft, and the wall thickness of the shaft. If too low a duroneter is used, the material tends to grip too much and he material tends to rip apart; it too high a durometer is used, the radial force required to drive the endoscope shaft without slippage is so high that the endoscope shaft becomes damaged.

The gears 126, 128 are affixed to a central shaft 212, 214, respectively by conventional screws 129, 131. End bearings 216, 218 and flange bearing 220, 220 are provided, together with an end plug 224,; 226, 227, as shown. The housing 230, here machined or cast anodized aluminum is formed with the base portion of section 106 at the distal end thereof, adapted to store the wheel 110 and, at the proximal end thereof, the motor assembly 130. The housing 230 is formed with a fork shaped mounting flange 234 which provides one of a pair of yoke sections. The cam 136 is stored within the fork of the mounting flange 234 and a pair of mating mounting blocks 236, 238, block 238 being shown in FIG. 6C. The pair of blocks 236, 238 together provide the second one of the yokes. When blocks 236, 238 are fastened together by four screws 235, only two of such screws 235 being shown, the cam 136 rotates between the mounting blocks 236, 238 and within the fork shaped mounting flange 234 by a pin 138, not shown in FIG. 8 but shown in FIGS. 7A and 7B). A handle 240 is fit into a slot 242 formed in the cam 136. Covers 241, 243 for section 106, 108, respectively are fastened by screws, not numbered. A stainless steel dowel 109' is inserted along axis 109 (FIGS. 6A, 6B, 7A, 7B) to provide the pivot axis for the sections 106, 108.

The assembly 237 is used to pivotally mount stem 140 to the housing 230. Thus, the assembly 237 includes a shaft 237a, a spring 237b, a spring plug 237c, a stainless steel knob 237d, and a head set screw 237e, arranged as shown to enable the stem 140 to pivot.

Figure 9:
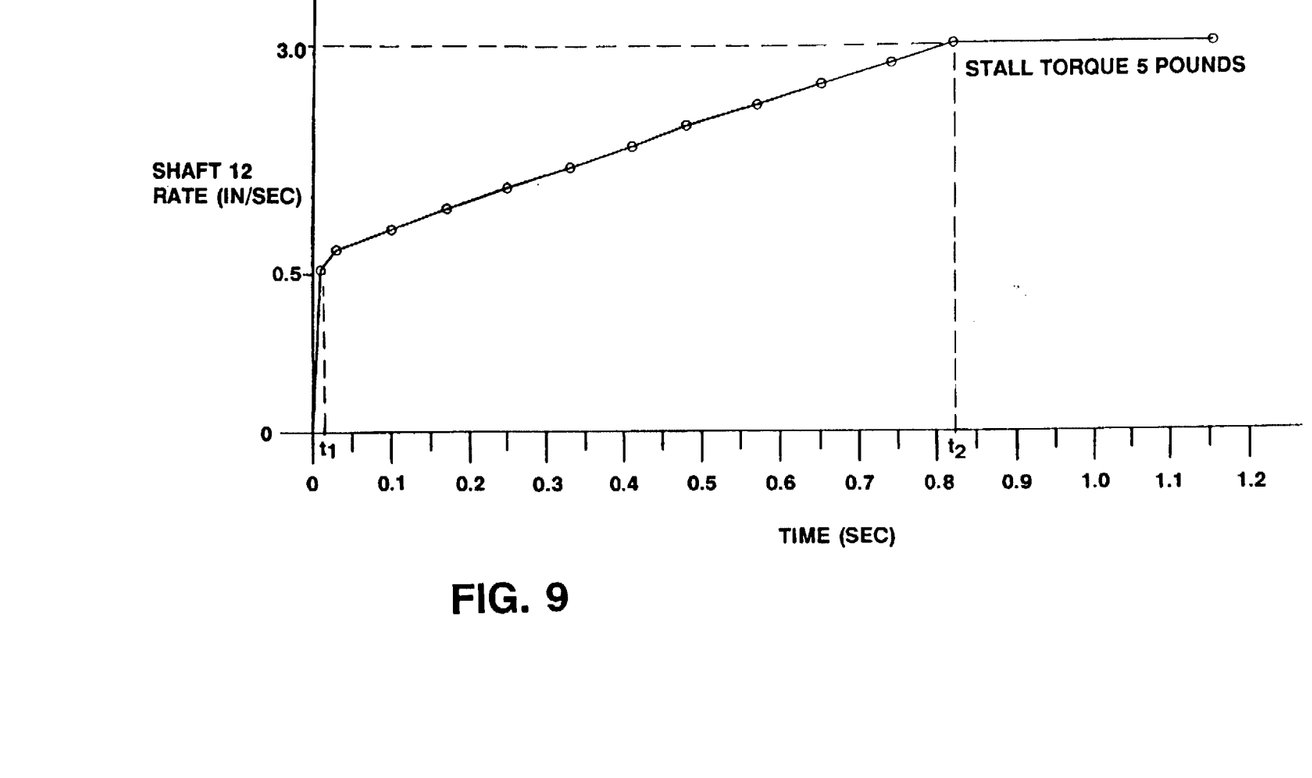
FIG. 9 is a curve showing the time history of the speed of a motor used in the device of FIGS. 6A–6B to move the instrument.

Referring now to FIG. 9, a time history of the speed profile of the motor speed is shown. From time zero to time $t_1$, here about 0.03 seconds the motor speed increases to a rate which moves that shaft 12 to a rate of ½ inch per second. After the motor speed changes to increase the shaft movement rate to 3 inches per second at time $t_2$, here about 0.8 seconds. Thereafter, the shaft rate remains at 3 inches per second, as shown. Thus, the motor driving speed follows a ramp characteristic: the motor drives the shaft slowly at first, and then speeds up after a while. The slow driving speed improves the surgeon's ability to control the position of the endoscope.

Other embodiments are within the scope of the claims. For example, instead of using a pivotal clamp, the clamp may be formed of two separate sections, one including the motor and one of the drive wheels and the other including the other drive wheel. When the two sections are not fastened together, the clamp is in the open position; on the other hand when the two sections are fastened together, the clamp is in the closed position.

A voice-activated remote actuator may also be employed to activate the motor to drive in forward and reverse directions.

An additional drive wheel may be disposed in the housing of the instrument-positioning device to selectively engage the laparoscope to rotate the laparoscope about its axis. This feature would provide a distinct advantage for use with a laparoscope in which the view port is not aligned with the longitudinal axis.

Additional configurations of the invention include providing for remote-controlled three-dimensional positioning of a medical instrument.

What is claimed is:

1. A remote-control device for selectively positioning a medical instrument within a predetermined region of space, said medical instrument having an axially elongated shaft defining an axis, said device comprising:

a clamp having a first section and a second section, the first and second sections being pivotally mounted to enable the clamp to be placed in an open position wherein the shaft of the medical instrument can laterally pass between the first and second sections of said clamp, and in a closed position wherein the shaft of the medical instrument is laterally held between the first and second sections of said clamp, each section having:

a drive wheel rotatably coupled to said section and having a surface exposed for frictional engagement with the shaft of the medical instrument, said drive wheel being rotatable about an axis that is perpendicular to the axis defined by the medical instrument so that when the surface of said drive wheel engages with the shaft of the medical instrument rotation of the drive wheel moves the medical instrument in a direction along the axis defined by the medical instrument, the surface of said wheel being formed from a material having an elastomeric characteristics for grasping the shaft; and wherein each drive wheel has a coupling gear mounted to rotate with the drive wheel, with the clamp in the closed position, the coupling gear of the first section engaging the coupling gear of the second section, and a motor housed in the first section of the clamp for directly driving the drive wheel of the first section.

2. The device recited in claim 1 wherein, with the clamp in the open position, the coupling gear of the first section and the coupling gear of the second section are positioned and configured such that portions of teeth of the coupling gear of the first section and the coupling gear of the second section remain engaged with each other thereby preventing the coupling gears from becoming misaligned when the clamp is placed in the closed position.

3. The device recited in claim 2 including an eccentric cam, pivotally mounted to one of the first and second sections of the clamp to lock the first and second sections of the clamp in the closed position.

4. The device recited in claim 3 wherein the cam is configured to place the clamp in the closed position when the cam is rotated and a camming surface thereof is urged against the second section to cause the second section to rotate and, after completion of rotation of the cam, thereby lock the clamp in the closed position.

5. The device recited in claim 1 wherein, said shaft defines a 360 degree outer circumference and the surface of each drive wheel extends for 30–35 degrees of the 360 degrees.

6. The device recited in claim 5 wherein portions of the drive wheels which grasp the shaft is a material having a durometer of between 40–60.

7. The device recited in claim 6 wherein the durometer is 50.

8. The device recited in claim 1 wherein the motor is configured to drive the shaft initially at a first speed, and following a predetermined time at the first speed, the motor is configured to drive the shaft at a second speed faster than the first speed.

9. The device recited in claim 8 wherein the first speed is ½ inch per second.

10. The device recited in claim 8 wherein the second speed is 3 inches per second.

11. The device recited in claim 8 wherein the predetermined time is 0.03 seconds.

12. A remote-control device for selectively positioning a medical instrument within a predetermined region of space, said medical instrument having an axially elongated shaft defining an axis, said device comprising:

a clamp having a first section and a second section, the first and second sections being pivotally mounted to enable the clamp to be placed in an open position wherein the shaft of the medical instrument can laterally pass between the first and second sections of said clamp, and in a closed position wherein the shaft of the medical instrument is laterally held between the first and second sections of said clamp, each section having:

a drive wheel, rotatably coupled to each section and having a surface exposed for frictional engagement with the shaft of the medical instrument, each drive wheel having a coupling gear mounted to rotate with the drive wheel, with the clamp in the closed position, the coupling gear of the first section engaging the coupling gear of the second section, and a motor housed in the first section of the clamp, an output shaft of the motor being directly connected to a central shaft of the drive wheel of the first section for directly driving the drive wheel of the first section.

13. A remote-control device for selectively positioning an endoscope within a predetermined region of space, said endoscope having an axially elongated shaft defining an axis, said device comprising:

a clamp having a first section and a second section, said clamp being characterized by an open position wherein the shaft of the endoscope can laterally pass between the first and second sections of said clamp, and by a closed position wherein the shaft of the endoscope is laterally held between the first and second sections of said clamp, each section having:

a drive wheel rotatably coupled to said section and having a surface exposed for frictional engagement with the shaft of the endoscope, said drive wheel being rotatable about an axis that is perpendicular to the axis defined by the endoscope so that when the surface of said drive wheel engages with the shaft of the endoscope rotation of the drive wheel moves the endoscope in a direction along the axis defined by the endoscope, the surface of the wheel being formed from a material having an elastomeric characteristics for grasping the shaft; and wherein each drive wheel has a coupling gear mounted to rotate with the drive wheel, with the clamp in the closed position, the coupling gear of the first section engaging the coupling gear of the second section, and a motor housed in the first section of the clamp for directly driving the drive wheel of the first section.

14. The device recited in claim 13 wherein, with the clamp in the open position, the coupling gear of the first section and the coupling gear of the second section are positioned and configured such that portions of teeth of the coupling gear of the first section and the coupling gear of the second section remain engaged with each other thereby preventing the coupling gears from becoming misaligned when the clamp is placed in the closed position.

15. The device recited in claim 14 including an eccentric cam, pivotally mounted to one of the first and second sections of the clamp to lock the first and second sections of the clamp in the closed position.

16. The device recited in claim 15 wherein the cam is configured to place the clamp in the closed position when the cam is rotated and a camming surface thereof is urged against the second section to cause the second section to rotate and, after completion of rotation of the cam, thereby lock the clamp in the closed position.

17. The device recited in claim 13 wherein, said shaft defines a 360 degree outer circumference and the surface of each drive wheel extends for 30–35 degrees of the 360 degrees.

18. The device recited in claim 17 wherein portions of the drive wheels which grasp the shaft is a material having a durometer of between 40–60.

19. The device recited in claim 18 wherein the durometer is 50.

20. A remote-control device for selectively positioning a medical instrument within a predetermined region of space, said medical instrument having an axially elongated shaft defining an axis, said device comprising:

a clamp having a first section and a second section, said clamp being characterized by an open position wherein the shaft of the medical instrument can laterally pass between the first and second sections of said clamp, and by a closed position wherein the shaft of the medical instrument is laterally held between the first and second sections of said clamp, each section having:

a drive wheel rotatably coupled to each section and having a surface exposed for frictional engagement with the shaft of the medical instrument, each drive wheel having a coupling gear mounted to rotate with the drive wheel, with the clamp in the closed position, the coupling gear of the first section engaging the coupling gear of the second section, and a motor housed in the first section of the clamp, an output shaft of the motor being directly connected to a central shaft of the drive wheel of the first section for directly driving the drive wheel of the first section.

* * * * *